United States Patent [19]

Shell

[11] Patent Number: 4,680,171

[45] Date of Patent: Jul. 14, 1987

[54] VISUALIZATION OF A BLOODSTREAM CIRCULATION WITH BIODEGRADABLE MICROSPHERES

[76] Inventor: William Shell, 956 Chantilly Rd., Los Angeles, Calif. 90077

[21] Appl. No.: 712,038

[22] Filed: Mar. 15, 1985

[51] Int. Cl.[4] ............................................. A61K 49/04
[52] U.S. Cl. ..................................................... 424/5
[58] Field of Search ........................................... 424/5

[56] References Cited

U.S. PATENT DOCUMENTS 3,984,571 10/1976 Chen ......................................... 424/5
4,192,859 3/1980 MacKaness et al. ..................... 424/5
4,285,928 8/1981 Wada et al. .

FOREIGN PATENT DOCUMENTS 0032829 2/1983 Japan ....................................... 424/5

Primary Examiner—Frederick E. Waddell
Attorney, Agent, or Firm—Robert J. Schaap

[57] ABSTRACT

An inexpensive and easy to use method of visualizing an arterial circulation using biodegradable microspheres dyed with an X-ray absorbent material, which enables the diagnosis of pulmonary embolism, is provided. The microspheres may be comprised of a variety of materials, including human albumin, and may be dyed with a number of X-ray absorbent materials, including hypaque-sodium and potassium iodide. The microspheres are injected into bloodstream at a particular location such that they travel through the desired arterial circulation, where they become lodged. Upon exposure of the arterial circulation to X-rays, blood vessels therein containing the microspheres will absorb the X-rays, causing them to show on a developed X-ray in contrast to other blood vessels and body tissue which do not contain the microspheres that transmit the X-rays. The microspheres are designed to dissolve into the bloodstream within fifteen to thirty minutes after their introduction, the X-ray dye being ultimately excreted from the body via the urine or metabolized by the liver.

3 Claims, No Drawings

VISUALIZATION OF A BLOODSTREAM CIRCULATION WITH BIODEGRADABLE MICROSPHERES

BACKGROUND OF THE INVENTION

1. Field of the Invention

This invention relates generally to the diagnosis of pulmonary embolism and, more particularly, to the diagnosis of pulmonary embolism using biodegradable microspheres dyed with X-ray absorbent or opaque material.

2. Brief Description of the Prior Art

Decreased blood flow to various organs is a danger faced by all mammals, particularly man. A decrease in blood flow to the lungs is especially dangerous, since it is in the lungs that oxygen is incorporated into the blood for distribution throughout the body.

A blood clot in the lungs, which is one cause of decreased blood flow, gives rise to a disease known as pulmonary embolism. This is one of the most difficult diseases to diagnose because the emboli can be small. The emboli are transparent to conventional X-rays and produce only non-specific symptoms.

In the current technology, diagnosis of pulmonary embolism is generally performed by a pulmonary anteriogram, a technique where a catheter is placed through the heart into the pulmonary artery. An X-ray opaque liquid dye (X-ray dye) is injected through the catheter into the lungs, after which an X-ray movie (angiogram) is used to visualize blood flow through the lungs.

There is also a non-invasive method to diagnose pulmonary embolism which utilizes biodegradable albumin aggregates labeled with radioactive technetium 99m. The technique involves injection of the aggregates into a vein allowing the aggregates to lodge in the lung. Visualization of the aggregates is performed by a nuclear camera which detects the radioactive emission or so-called "radiolabel".

The current technolgy for diagnosing pulmonary embolism is inadequate due to the fact that patients are hesitant to have this procedure performed routinely. Further, the insertion of a catheter into the heart and lungs is a surgical procedure, limiting use of this method to hospitals and requiring complex equipment to produce acceptable sequential images.

Use of radioactively labeled biodegradable albumin aggregates has several disadvantages. First, the method is very expensive to use because it is radioactively based. Reasons for these high costs include expensive radioactive measuring equipment and the necessity of protecting medical personnel from radiation exposure. Second, the radioactively labeled aggregates have a limited shelf-life, ranging from one week to several months. Even when the shelf-life is at the high end of this range, the continuous decay makes frequent recalibration of the testing apparatus necessary. Finally, this type of test is also limited to hospitals because of the expense of obtaining the proper equipment. Aside from the materials, the costs involved in minimizing radiation exposure for these individuals is substantial. Patients are also hesitant to undergo testing involving the insertion of radioactive materials into their bodies. All of these problems result in low usage of this type of test.

In addition to the disadvantages described above, the non-invasive radioactive tests have poor reliability because the resolution of the images is limited and small emboli cannot be detected. The patients must be flat for many minutes to allow sufficient radioactive disintegration to occur in order to provide enough information to create the image. Otherwise, small movement blurs the image thereby limiting image isolation.

Because of the problems and disadvantages associated with current methods of diagnosing pulmonary embolism, there is substantial under-utilization of pulmonary embolism testing in relation to the frequency of occurrence of the disease. What is needed, therefore, is a method of diagnosing pulmonary embolism that is accurate, inexpensive to use, inoffensive to patients and capable of being used in a traditional doctor's office. The present invention satisfies these needs and provides other related advantages.

SUMMARY OF THE INVENTION

The present invention resides in the use of biodegradable microspheres labled with X-ray absorbent material, often referred to as X-ray "opaque" material which can be used to visualize an arterial circulation, thereby enabling the diagnosis of pulmonary embolism and other maladies, as well as in a method of preparing such microspheres. Diagnosis of pulmonary embolism using the present invention is accurate and easy to perform, allowing testing to be conducted in a doctor's office. The present method is also relatively inexpensive and poses no health problems for medical personnel since there is an absence of radioactivity.

More specifically, the method of the present invention involves labeling biodegradable microspheres with X-ray absorbent material, making the microspheres themselves X-ray absorbent or so-called "X-ray opaque". An "X-ray absorbant" substance will absorb X-rays, and will therefore appear as a white area on a developed X-ray film; whereas a tissue or area which transmits X-rays will appear dark on the X-ray film.

The X-ray opaque microspheres are injected into a peripheral vein and are carried to the lungs, where they become lodged in small blood vessels. If a blood clot is present in the lungs, the microspheres will not be carried to blood vessels that are downstream of the blood clot. The lungs are then X-rayed and the resulting X-ray image is examined. The majority of blood vessels in the lungs will show as white areas in the X-ray because of the presence of the X-ray absorbent microspheres lodged in the small capillaries. The blood clot and any area of the lungs to which blood flow is restricted, whereby being devoid of X-ray laden microspheres, however, will show as dark areas on the X-ray, since these areas of the lungs will have transmitted the X-rays.

The microspheres are composed of a biodegradable material that dissolves into the blood within fifteen to thirty minutes after their introdution. The dissolved microspheres are degraded in the body and the X-ray dye excreted out of the body via the urine.

The microspheres used with the present invention are biodegradable and are designed to dissolve into the bloodstream within fifteen to thirty minutes after their introduction. They may be of various compositions, including albumin, and starch, with albumin being preferred. The term "microsphere" is used to represent generally spherically shaped particles with each particle ranging in size from about 9 u to about 100 u and preferably from about 10 u to about 50 u. A "uniform" size grouping of microspheres used with the present invention may preferably contain microspheres ranging in size anywhere from 10 u to 50 u in diameter.

Albumin microspheres used with the present invention are prepared by injecting droplets of an albumin solution into rapidly stirred oil. The microspheres are stablized either by heating or by cross-linking with glutaraldehyde, and are washed with ethyl ether or petroleum ether and then dried by a suitable drying agent or drying mechanism. The ultimate size of the microspheres is controlled by the speed with which the oil is stirred, the size of the albumin droplets and by whether the albumin solution is pre-dispersed in oil by sonication.

X-ray absorbent material is mixed into the initial solution before droplet injection so as to make the microspheres themselves X-ray absorbent. Various materials may be used for this purpose, including potassium iodide (KI) and hypaque-sodium, the latter being preferred. Hypaque-sodium is a soluble solid having four-iodine atoms per molecule, making it ideal for use with the microspheres of the present invention.

The X-ray absorbent microspheres are injected into a peripheral vein and allowed a short time to circulate through the lungs. A chest X-ray is taken and examined. The presence of the X-ray absorbent microspheres allows visualization of the arterial circulation within the lungs, as blood vessels in the lungs containing the microspheres will show up as white areas on the X-rays, in contrast to the surrounding tissue structure. If a blood clot is present, the clot will transmit the X-rays and will therefore show as a dark area, in contrast to the other blood vessels in the lungs. Similarly, any area of the lungs to which blood flow has been restricted as a result of the blood clot will also show as dark areas in contrast to the other blood vessels in the lungs containing X-ray absorbent microspheres.

The microspheres used with the present invention are composed of albumin or other biodegradable material so there will be no residue or lasting physiological effects to the body once the test is concluded. The microspheres are designed to dissolve into the bloodstream within fifteen to thirty minutes after introduction into the body, the exact time period being a function of their composition and size. This time period is sufficient to conduct the test of the present invention, but not too long so as to cause any damage to the lungs. After dissolution, the X-ray dye is passed out of the body in the urine and the albumin is degraded by the liver.

The arterial circulation visualization method of the present invention, which enables diagnosis of pulmonary embolism, provides dynamic advantages over the X-ray movie and radioactive methods used currently. As compared to radioactive albumin aggregates, costs with the present invention are significantly decreased due to the lack of necessity for radiation detection and protective equipment. The present method is much safer because there is no exposure of the patients and medical personnel to harmful radioactivity, and is also much more reliable than radioactively based methods. As compared to invasive techniques, such as an injection of X-ray absorbent dye and visualization using an X-ray movie, the present method is much less offensive to patients and is simplier to perform. Unlike both radioactively based and X-ray dye injection methods, the method of the present invention may be used to diagnose pulmonary embolism in a doctor's office.

Other features and advantages of the present invention will become apparent from the following detailed description which illustrates, by way of example, the principles of the invention.

DETAILED DESCRIPTION OF THE PREFERRED EMBODIMENT

The present invention is embodied in the use of biodegradable micropheres dyed with X-ray absorben material to visualize an arterial circulation, thereby enabling the diagnosis of pulmonary embolism, as well as in methods of preparing such microspheres. More specifically, the method of the present invention involves dying microspheres composed of albumin or other materials with an X-ray absorbent material so as to make the microspheres themselves X-ray absorbent. These X-ray absorbent or opaque microspheres are then injected into the bloodstream of a patient and are distributed to the arterial circulation area to be visualized. An X-ray of the area is taken and developed. If the arterial circulation area is the lungs, for example, blood vessels in the lungs filled with X-ray absorbent microspheres will show as white areas on the X-ray, while a blood clot and blood vessels of the lungs to which blood flow has been restricted will have transmitted the X-rays and consequently will show as dark areas. Within fifteen to thirty minutes after injection of the X-ray absorbent microspheres into the bloodstream, they are dissolved and subsequently excreted from the body via the urine, leaving no lasting physiological effects.

When used to diagnose pulmonary embolism, the method of the present invention provides significant advantages over the use of X-ray dye and radioactivity treated biodegradable aggregates, which are currently the most common methods used for such diagnosis. The present method poses no health hazards to medical personnel and patients and costs significantly less to use because there is no need to protect medical personnel from radioactivity, or to purchase radioactivity measuring equipment. The present method is also less complex then current methods in that simple X-rays are used to conduct the test and there is no insertion of foreign materials into the heart and lungs. This allows the method of the present invention to be used to diagnose pulmonary embolism in a doctor's office. Further, the present method is much more reliable than a radioactively based method.

The term "microsphere" is used to represent a particle ranging in size from about 9 u to about 100 u and preferably about 10 u to about 50 u in diameter, as previously stated. A particular group of "uniformly" sized microspheres may include particles having a diameter anywhere in this range.

The microspheres of the present invention may be composed of any biodegradable material that is capable of being formed into microspheres in the desired size range. Possible biodegradable materials include, but are not limited to, human albumin, and starch, with human albumin being preferred.

The starches which may be used to form the microspheres of the present invention are usually polysaccharides which are biodegradable by blood stream ehzymes. Other materials which may be used to form the microspheres are certain fats, such as lipid particles, triglycerides, lyphoproteins and free fatty acid lipids, as well as mixtures of the foregoing.

As shown in Example 1, X-ray absorbent albumin or other microspheres may be prepared by injecting droplets of a congealing solution containing albumin and hypaque-sodium into cotton seed oil that is being rapidly stirred. The congealing solution is one which causes the albumin or other biodegradable material to congeal upon contact. A large number of oils may be used in place of cotton seed oil and include, for example, linseed oil, maleic acid, etc. In effect, the congealing solution can be any lipid liquid form. A congealing solution enables formation of the droplets, inasmuch as the protein materials which are introduced into the lipid congealing solution are entirely immiscible and thereby cause the protein biodegradable materials to form into the small microspheres.

The microspheres may be washed, typically with alcohols and preferably lower molecular weight alcohols. Thus, 95% ethanol, denatured isopropyl alcohol, etc. may be used. Highly effective washing solutions have been found to be certain ethers, such as ethyl ether or petroleum ether. The microspheres are stablized either by heating, as shown in Example 1, or by cross-linking as for example with glutaraldehyde. The microspheres are then dried, by any rapidly evaporating alcohol, as for example, ethyl ether as mentioned above. The stablized microspheres may also be dried by heating in air or drying in a vacuum.

The size of the microspheres are determined to some extent by the washing and drying steps. The washing in the various alcohols should take place no longer than about 10 minutes. Moreover, drying should take place for about 30 minutes to about 60 minutes at a temperature within the range of about 50 degrees F to about 70 degrees F.

The dried albumin microspheres have the X-ray absorbent hypaque-sodium incorporated into them, making them X-ray absorbent. Bones and tissues within the human body absorb X-rays, which allows them to be viewed using conventional X-ray techniques. A substance that is "X-ray absorbent" or "X-ray opaque" also absorbs X-rays and is therefore visible using X-ray techniques. Therefore, X-ray absorbent materials show as white areas on a developed X-ray film. Thus, for example, the normal human lung will appear dark in an X-ray film. However, when the X-ray absorbed microspheres appear in the lung capillaries, those regions will appear white on a X-ray film due to the fact that they absorb the X-rays. If an embolism is present, the regions downstream of the embolism which do not receive the X-ray absorbed microspheres will thereby also appear to be dark on an X-ray film.

Potassium iodide (KI) may also be used to render the albumin microspheres X-ray opaque. The resulting albumin microspheres have KI crystals on their surface and partially incorporated into their structure.

Ions other than potassium iodide can also be used. For example, iron is also an effective X-ray absorbent material. In accordance with the present invention, it has been found to be highly effective to use a combination of both potassium iodide and iron. In this way, using multiple ions, it is possible to reduce the concentration of X-rays to a point where they will be microspheres X-ray absorbent.

Diagnosis of pulmonary embolism, as shown in Example 2, first involves injecting X-ray opaque microspheres, such as those prepared in Example 1, into a peripheral vein. The microspheres travel to the lungs where they become lodged in the blood vessels. If a blood clot is present in the lungs, no microspheres will flow to areas of the lungs that are directly downstream of the clot.

Within fifteen minutes of injection of the X-ray opaque microspheres, a chest X-ray of the patient is taken and developed. Areas of the lungs containing the X-ray opaque microspheres will show on the developed X-ray as white areas, as the microspheres in those blood vessels will absorb the X-rays. Areas of the lungs to which blood flow has been restricted by the blood clot will show as dark areas on the developed X-ray because they will have transmitted the X-rays. The blood clot itself, of course, will also show as a dark area.

Even is there is no blood clot present in the lungs, the method of the present invention enables visualization of the arterial circulation of the lungs. Arterial circulations in other parts of the body can also be viewed by varying the point of injection into the bloodstream proximal to the organ.

The microspheres can be injected into the body at any desired location in order to enable X-ray inspection of the desired regions of the body. For example, when using the method of the present invention to determine the presence of a blood clot in the lungs, the microspheres are introduced into a vein for return to the heart. These microspheres will pass through the heart and move directly into the lungs. In this way, the microspheres, which are slightly larger than red blood cells, will be captured in the small capillaries of the lungs.

If it is desired to X-ray analyze a hand or other portion of the body, the microspheres would be injected into an artery upstream of the organ or other body tissue which is to be examined.

Within fifteen to thirty minutes after introduction into the bloodstream, the microspheres of the present invention are totally biodegraded by the blood and become dissolved therein. The exact dissolution time is a function of the composition and size of the microspheres. This time period is sufficiently short that no physiological damage to the patient results. The dissolved microspheres are ultimately passed out of the body in solution via the urine.

The following examples will serve to illustrate the present invention in accordance with preferred embodiments.

EXAMPLE 1

Preparation of X-ray Opaque Microspheres Using Albumin and Hypaque-Sodium

Human albumin (110 mgs) was dissolved in 3 mls of distilled water, to which hypaque-sodium (500 mg/100 gm albumin) was added. Cotton seed oil (100 mls) was heated to 40 degrees C. in a 150 ml beaker on a hot plate with high-speed mechanical stirring using a polyethylene three-blade propeller in an Eberbach Con-Torque stirring motor. The albumin-hypaque-sodium solution was injected into the oil by drop-wise addition from a syringe with a 25 gauge needle, the oil being stirred and heated continuously during this addition. The addition of the albumin-hypaque-sodium solution raised the temperature of the oil about 20 degrees C. Stirring and heating were continued until the oil reached 115 degrees C., in approximately fifteen minutes. The temperature was maintained at 115 degrees C. for ten minutes.

During the addition of the albumin-hypaque-sodium solution, the stirred emulsion first become very turbid and then cleared as the albumin droplets dehydrated. The preparation felt gritty when a drop was rubbed between fingers.

After cooling of the emulsion, the microspheres settled rapidly and most of the supernatant oil was decanted. The remainder of the suspension was centrifuged and the oil aspirated. The microspheres were washed four times with ethyl ether and air dried in a fume hood.

Alternative materials and techniques are available at various stages of the above process. For example, potassium iodide (KI) substituted for hypaque-sodium at the same concentration yielded a product in which KI crystals were present on the surface of the microspheres and were partially incorporated into the interior of the microspheres. Stabilization of the microspheres, accomplished by heating in the above-described process, may also be accomplished by cross-linking the microspheres with glutaraldehyde. The microspheres may be washed with petroleum ether instead of ethyl ether.

EXAMPLE II

The arterial circulation of a dog was visualized by injecting 5 mgs of X-ray labeled microspheres (100 micron size) into the superior vena cava. During and following the injection, the X-ray images of the dogs right heart, pulmonary arteries, and lungs were recorded on video tape. The X-ray images were produced using standard fluoroscopy equipment interfaced to a television camera and video recorder.

Following the injection, the right atrium, right ventricle and pulmonary artery became radio-opaque as the microspheres passed through those structures. The microspheres then lodged in the pulmonary arterioles of approximate 100 u size. Thus, a random sample of the entire distribution of 100 u arterioles became visualized as the microspheres lodged in those arterioles. The course of the arteries, which were previously radio-translucent, could be visualized when rendered radio-opaque by the microspheres. The arterioles remained visable for about 30 minutes and became radio-translucent as the microspheres dissolved. A single X-ray film at 10 minutes after injection would visualize the pulmonary circulation. A pulmonary embolism would be visualized as a defect in the expected distribution of blood vessels; e.g. you could see a dark area where the remaining lung marked with radio-opaque microspheres would be white as seen in the fluoroscopic images.

Thus there has been described a unique and novel method of enabling visualization of arterial circulation as well as a method of diagnosing pulmonary embolism and a method of preparing biodegradable X-ray opaque microspheres which fulfills all of the objects and other advantages which have been sought. It should be understood that many changes, modifications, variations, and other uses and applications of the described methods and the articles will become apparent to those skilled in the art after considering this specification. Therefore, any and all such changes, modifications, variations and other uses and applications are deemed to be covered by the spirt and scope of this invention.

What is claimed is:

1. A method of visualizing an arterial circulation in the bloodstream of a subject comprising the steps of:
    (a) selecting a quantity of microspheres bearing an x-ray absorbent material which will enable generation of an x-ray image and for a desired duration when injected into the bloodstream of a subject;
    (b) injecting biodegradable x-ray absorbent microspheres into the bloodstream of the subject at a point in the subject's circulatory system such that said microspheres are carried in the bloodstream to an arterial circulation area sought to be visualized and which remain in the circulatory system for a time sufficient to be subjected to X-ray imaging;
    (c) subjecting said arterial circulation area to X-rays to form an X-ray image of said arterial circulation area and causing the microspheres to absorb the X-rays to render them X-ray opaque for contrast against surrounding or adjacent tissue;
    (d) examining said X-ray image for the pressure of white areas on an X-ray film to represent the presence of said microspheres, which will enable visualization of said arterial circulation by means of the absorption of X-rays by said microspheres; and
    (e) thereafter permitting the microspheres to become degraded in the body after a period of time for visualization which is sufficient to enable X-ray imaging but which is not sufficiently long to create damage to the tissue in which the visualization of the arterial circulation is taking place.

2. A method as set forth in claim 1 wherein said microspheres have a size on the order of about 9 u to about 100 u in diameter.

3. A method as set forth in claim 1 wherein said arterial circulation is a pulmonary circulation.

* * * * *